United States Patent [19]

Engelhardt et al.

[11] Patent Number: 5,274,048
[45] Date of Patent: Dec. 28, 1993

[54] USE OF GLYCIDYL PHOSPHONATES AS CROSSLINKERS IN THE PREPARATION OF HYDROGELS

[75] Inventors: Fritz Engelhardt; Ulrich Riegel, both of Frankfurt; Hanss-Jerg Kleiner, Kronberg; Wolf-Dieter Müller, Hofheim, all of Fed. Rep. of Germany

[73] Assignee: Cassella AG, Frankfurt am Main, Fed. Rep. of Germany

[21] Appl. No.: 772,798

[22] Filed: Oct. 8, 1991

[30] Foreign Application Priority Data

Oct. 18, 1990 [DE] Fed. Rep. of Germany ....... 4033007

[51] Int. Cl.$^5$ .............................. C08F 8/40; C08J 3/24
[52] U.S. Cl. .................................... 525/340; 525/326.6; 525/329.8; 525/330.4; 525/193; 525/287; 526/278
[58] Field of Search ............... 525/326.6, 329.8, 330.4, 525/340; 526/278

[56] References Cited

U.S. PATENT DOCUMENTS 4,259,117  3/1981  Yamauchi et al. ................... 526/278

FOREIGN PATENT DOCUMENTS 0997820  7/1965  United Kingdom ............... 525/340

OTHER PUBLICATIONS

*Chemical Abstracts;* 99:45968g (1983), p. 486—Brainin et al. (Russ).
*Chemical Abstracts;* 68:94873p (1964),—Bloechl.

*Primary Examiner*—Paul R. Michl
*Assistant Examiner*—Andrew E. C. Merriam
*Attorney, Agent, or Firm*—Connolly and Hutz

[57] ABSTRACT

The present invention relates to the use of compounds of the general formula I

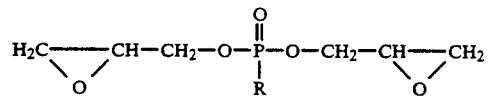

in which R denotes alkyl, alkenyl or aryl, which can be optionally substituted, as crosslinkers in the preparation of hydrogels, and to the hydrogels thus prepared and their use.

5 Claims, No Drawings

USE OF GLYCIDYL PHOSPHONATES AS CROSSLINKERS IN THE PREPARATION OF HYDROGELS

The present invention relates to the use of glycidyl phosphonates as crosslinkers in the preparation of hydrogels, and to the hydrogels thus prepared and their use.

For the preparation of hydrogels in aqueous solution, crosslinkers customarily employed are water-soluble compounds such as, for example, methylenebisacrylamide, bisacrylamidoacetic acid or alkenylphosphonic and phosphonic acid esters, but also poorly water-soluble compounds such as, for example, trimethylolpropane tri(meth)acrylate or tetraallyloxyethane.

The object of the present invention is to make available novel, water-soluble compounds which act as crosslinkers, by whose use hydrogels having improved properties with respect to gel strength and water retention ability are obtained.

This object is surprisingly achieved by the use of compounds of the general formula I

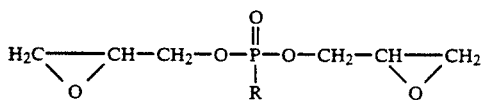

in which R denotes alkyl, alkenyl or aryl, which can be optionally substituted, as crosslinkers in the preparation of hydrogels.

Preferably used compounds of the general formula I

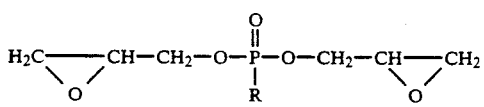

are those in which R denotes ($C_1$–$C_6$)-alkyl; ($C_3$–$C_8$)-cycloalkyl; a group of the general formula II

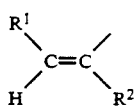

in which $R^1$ and $R^2$ independently of one another represent hydrogen or ($C_1$–$C_4$)-alkyl; or a group of the general formula III

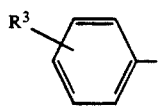

in which $R^3$ represents hydrogen, halogen or ($C_1$–$C_4$)-alkyl.

Alkyl groups can be straight-chain or branched. ($C_1$–$C_6$)-alkyl R in particular denotes methyl, ethyl, n-propyl, i-propyl, n-butyl, i-butyl, n-pentyl, i-pentyl, n-hexyl or i-hexyl, ($C_1$–$C_3$)-alkyl, however, being particularly preferred.

A particularly preferred ($C_3$–$C_8$)-cycloalkyl is cyclohexyl.

($C_1$–$C_4$)-alkyl $R^1$ or $R^2$ is particularly preferably methyl. $R^1$ and $R^2$, however, are very particularly preferably hydrogen.

The radical $R^3$ can be in the 2-, 3- or 4-position relative to the carbon-phosphorus bond.

($C_1$–$C_4$)-alkyl $R^3$ in particular denotes methyl, ethyl, n-propyl, i-propyl, n-butyl, i-butyl or tert-butyl. Halogen $R^3$ in particular denotes fluorine, chlorine, bromine or iodine.

$R^3$ particularly preferably denotes methyl or chlorine, very particularly preferably hydrogen.

The compounds of the general formula I can be prepared by known methods.

Thus, for example, U.S. Pat. No. 2,856,369 describes the reaction of diallyl phosphonates with peracids to give the corresponding diglycidyl phosphonates of the general formula I, Doklady Akad. SSSR, 155 (1964) 1137 describes the reaction of dichlorophosphonous acids with glycidol in the presence of base to give the corresponding diglycidyl phosphonites which, in turn, can be converted into compounds of the general formula I using oxidising agents such as $N_2O_4$.

Preferably, the compounds of the general formula I are prepared by reaction of the corresponding dichlorophosphonic acids with glycidol in the presence of base. The base is necessary for entraining the HCl formed in the reaction of dichlorophosphonic acid with glycidol, which leads to side reactions or secondary reactions. Zh. Obshch. Khim 116 (1984) 2404 recommends NaH as base, but nitrogen-containing bases are more frequently used. These in particular include tertiary amines such as trimethylamine, triethylamine, tripropylamine or tributylamine. U.S. Pat. No. 2,856,369 also recommends the use of pyridine. Trialkylamines are preferably employed, particularly preferably triethylamine.

Preferred solvents for these reactions are diethyl ether, methyl tert-butyl ether, benzene, toluene or xylenes, but other inert solvents and mixtures of various solvents are also suitable. For industrial purposes, particularly suitable solvents are those such as methyl tert-butyl ether, tetrahydrofuran, toluene or xylenes and their mixtures; toluene is particularly preferably employed.

The reactants and the required base are customarily employed in stoichiometric amounts, but excesses of base and/or glycidol may also be advantageous. Reasons for the preferred amounts used in each case can be of a process technology or application technology nature. Application technology reasons include, inter alia, purity criteria such as: colour, highest possible contents of active substance, lowest possible contents of by-products, lowest possible contents of starting compounds and lowest possible contents of hydrolysable and/or ionic chlorine. In the latter case, a lower excess, 1–20 mol %, preferably 1–5 mol %, of amine is frequently recommended.

For the reaction, a mixture of glycidol and base in the solvent used is customarily introduced, and the dichlorophosphonic acid is added dropwise either in substance, or dissolved in one of the solvents described. Other procedures are also possible. For example, the amine and the dichlorophosphonic acid can be introduced and the glycidol added dropwise. Continuous procedures are also possible. To this end, for example, streams of glycidol and amine are brought together with a stream of the appropriate dichlorophosphonic acid and thus made to react. One or both streams then contains the required solvent which is necessary in order to avoid blockages of the pipelines by precipitating amine hydrochloride.

After reaction is complete, the precipitated amine hydrochloride is customarily removed, for example by filtration or centrifugation. If a solvent-free product is required, the solvent is subsequently removed by distillation, optionally under reduced pressure. Further purification of the crude product thus obtained can be carried out by distillation under reduced pressure, either from the still, but preferably in a continuous manner by distillation via a thin film or short path evaporator.

The present invention also relates to water-swellable hydrogels based on (co)polymerised hydrophilic monomers or based on natural hydrophilic polymers, characterised in that they are crosslinked with a compound of the general formula I.

In the case of hydrogels based on (co)polymerised hydrophilic monomers, the compounds of the general formula I can even be added to the monomer mixture to be polymerised. However, the already polymerised so-called pre(co)polymers can also be crosslinked subsequently. Crosslinking is carried out by reaction of the epoxide groups of the compounds of the general formula I with the reactive groups, for example —COOH, —OH or —NHR, of the monomers or of the (co)polymers.

The compounds of the general formula I are preferably employed in amounts of 0.05 to 10% by weight, relative to the total monomer weight, or the total polymer weight respectively.

Suitable natural polymers which can be crosslinked with compounds of the general formula I to give hydrogels according to the invention can be employed either in the unpurified or in the purified form.

Particularly suitable, in particular, are polysaccharides, such as, for example, guar, carboxymethylhydroxypropyl guar, starch, cellulose, hydroxyethylcellulose and alginates.

Suitable copolymerisable hydrophilic monomers are in particular acrylic acid, methacrylic acid, crotonic acid, 2-acrylamido-2-methylpropanesulphonic acid and -phosphonic acid, vinylphosphonic acid, vinylphosphonic acid half-esters, their salts, acrylamide, N-vinylamides or mixtures thereof. Acrylic acid and its salts are preferred.

The polymerisation can be carried out in the homogeneous phase, for example in aqueous solution, as a so-called gel polymerisation. A further possibility for the synthesis of the hydrogels according to the invention is offered by precipitation polymerisation from organic solvents, such as, for example, alcohols, preferably tert-butanol, or hydrocarbons such as hexane or cyclohexane.

The polymerisation can be initiated by free-radical formers such as, for example, organic or inorganic peroxides and azo compounds. Examples are benzoyl peroxide, tert-butyl hydroperoxide, cumene hydroperoxide, $(NH_4)_2S_2O_8$, $K_2S_2O_8$, $H_2S_2O_8$, $H_2O_2$ or azodiisobutyronitrile. Redox systems are also outstandingly suitable as polymerisation initiators.

Finally, polymerisation can also be initiated by energy-rich radiation.

If the compound of the general formula I is only added to a non-crosslinked pre(co)polymer, this is as a rule carried out before drying by homogeneous mixing, for example by kneading an aqueous polymer gel in a kneader. Spraying dilute solution onto a polymer powder is also possible; a subsequent temperature treatment in this case is not absolutely necessary, but accelerates the crosslinking reaction.

The hydrogels according to the invention are outstandingly suitable as absorbents for aqueous fluids, for the formulation of cosmetic preparations, as strengtheners and/or binders of fibrous surface structures containing reactive groups and as drilling muds and cement slurries in oil production.

For use as so-called "super absorbing polymers" (SAP) for use in hygiene articles, for example nappies, tampons or sanitary towels, hydrogels according to the invention based on acrylic acid are particularly suitable, it being possible for these to be partially present as the alkali metal or ammonium salt. Neutralisation can be carried out either before or after polymerisation.

Hydrogels according to the invention based on polysaccharides are also outstandingly suitable for use as SAP.

As the compounds of the general formula I are completely soluble both in water and in organic solvents, water-swellable hydrogels according to the invention having a more homogeneous network than compounds of the prior art can be obtained. As a result, the hydrogels also have high gel strength in addition to high absorption capacity.

By subsequent crosslinking with compounds of the general formula I of already previously crosslinked polymers, which are intended for use as SAP, their performance can be substantially improved with respect to absorption under pressure.

A further advantage of the compounds of the general formula I is their biological degradability.

EXAMPLE 1

Synthesis of Diglycidyl Methanephosphonate (IV)

940 g of toluene are cooled to −5° C. and 148 g (2.0 mol) of glycidol and 213 g (2.1 mol) of triethylamine are subsequently added. 133 g (1.0 mol) of methanedichlorophosphonic acid dissolved in 60 g of toluene are added dropwise with vigorous stirring, in the course of 1 to 2 hours, at an internal temperature between −5° and 0° C. The mixture is subsequently stirred at 0° C. for 15 hours and the triethylamine hydrochloride formed is then filtered off with suction. It is washed with toluene and the filtrate is freed from toluene by distillation in vacuo. The residue is distilled via a short path evaporator at 1 mbar and a bath temperature of 175° C. 198 g of diglycidyl methanephosphonate are obtained, corresponding to a yield of 95%. The boiling point is determined by means of a distillation experiment: 114°–115° C./0.1 mbar. The product is obtained as a diastereomer mixture.

$C_7H_{13}O_5P$ (208.2): 
calc. 40.38% C, 6.29% H, 14.88% P.
found: 40.4% C, 6.1% H, 14.7% P.

EXAMPLE 2

Synthesis of Diglycidyl Propanephosphonate (V)

1000 g of toluene are cooled to −5° C. and 148 g (2.0 mol) of glycidol and 213 g (2.1 mol) of triethylamine are subsequently added. 161 g (1 mol) of propanedichlorophosphonic acid (technical isomer mixture, consisting of about 95% n-propyl and about 5% isopropyl isomers) are added dropwise with vigorous stirring, in the course of 1 to 2 hours, at an internal temperature between −5° and 0° C. The mixture is subsequently stirred at 0° C. for 15 hours and the triethylamine hydrochloride formed is then filtered off with suction. It is washed with toluene and the filtrate is freed from toluene by distillation in vacuo. The residue is distilled via a short path evaporator at 1 mbar and a bath temperature of 185° C. 227 g of diglycidyl propanephosphonate are obtained, corresponding to a yield of 95%. The boiling point is determined by a distillation experiment: 115°-124° C./0.04 mbar. The product is obtained as a diastereomer mixture.

$C_9H_{17}O_5P$ (236.2):
calc.: 45.77% C, 7.25% H, 13.1% P.
found: 45.5% C, 7.3% H, 13.0% P.

EXAMPLE 3

Synthesis of Diglycidyl Vinylphosphonate (VI)

1000 g of toluene are cooled to −5° C. and 148 g (2.0 mol) of glycidol and 213 g (2.1 mol) of triethylamine are subsequently added. 145 g (1.0 mol) of vinyldichlorophosphonic acid are added dropwise with vigorous stirring, in the course of 1-2 hours, at an internal temperature between −5° and 0° C. The mixture is subsequently stirred at 0° C. for 15 hours and the triethylamine hydrochloride formed is then filtered off with suction. It is washed with toluene and the filtrate is freed from toluene by distillation in vacuo. The residue is distilled via a short path evaporator at 0.1 mbar and a bath temperature of 150° C. 203 g of diglycidyl vinylphosphonate are obtained, corresponding to a yield of 92%. The product is obtined as a diastereomer mixture.

$C_8H_{13}O_5P$ (220.2):
calc.: 43.64% C, 5.05% H, 14.07% P.
found: 43.7% C, 6.0% H, 13.9% P.

EXAMPLE 4

Synthesis of Diglycidyl Benzenephosphonate (VII)

1000 g of toluene are cooled to −5° C. and 148 g (2.0 mol) of glycidol and 213 g (2.1 mol) of triethylamine are subsequently added. 195 g (1.0 mol) of benzenedichlorophosphonic acid are added dropwise with vigorous stirring, in the course of 1-2 hours, at an internal temperature between −5° and 0° C. The mixture is subsequently stirred at 0° C. for 15 hours and the triethylamine hydrochloride formed is then filtered off with suction. It is washed with toluene and the filtrate is freed from toluene by distillation in vacuo. The residue is distilled via a short path evaporator at 0.15 mbar and a bath temperature of 200° C. 251 g of diglycidyl benzenephosphonate are obtained, corresponding to a yield of 93%. The boiling point is determined by a distillation experiment: 170°-175° C./0.1 mbar.

$C_{12}H_{15}O_5P$ (270.2):
calc.: 53.34% C, 5.60% H, 11.46% P.
found: 51.1% C, 5.6% H, 11.3% P.

EXAMPLE 5

4780 g of demineralised water are introduced into a polyethylene vessel which is well insulated by foamed synthetic material and has a capacity of 10 l, 1696 g of sodium bicarbonate are suspended therein and 1994 g of acrylic acid are slowly metered in in such a way that frothing over of the reaction solution is avoided, the latter being cooled to a temperature of about 5°-3° C. 6 g of the compound V (R=$C_3H_7$), prepared according to Example 2, and 10 g of a sodium diisooctylsulphosuccinate (Rewopol V 2133 from REWO, Steinau) are then added. The initiators, a redox system consisting of 2.2 g of 2,2'-azobisamidinopropane dihydrochloride, dissolved in 20 g of demineralised water, 4 g of potassium peroxodisulphate, dissolved in 150 g of demineralised water and 0.4 g of ascorbic acid, dissolved in 20 g of demineralised water are added successively at a temperature of 4° C. and the mixture is stirred. The reaction solution is then allowed to stand without stirring, a solid gel being formed by commencing polymerisation, in the course of which the temperature rises to about 89° C. This gel is then mechanically comminuted, dried at temperatures above 80° C. and ground.

The product described was incorporated in a conventional manner into a baby nappy and is in this case distinguished by a particularly good liquid retention.

EXAMPLE 6

The procedure is completely analogous to Example 5, only 6.0 g of the compound VI (R=CH=$CH_2$), prepared according to Example 3, are now employed. The product resulting in this case is also outstandingly suitable for use in baby nappies and is distinguished by good liquid retention.

EXAMPLE 7

1287 g of demineralised water cooled to 15° C. are introduced under adiabatic conditions into a 1.5 l cylindrical wide-necked reaction flask and 255 g of acrylic acid and 1.28 g of tetraallyloxyethane are dissolved therein. Nitrogen is introduced into the monomer solution (about 2 l/min. for about 20 min.) in order to reduce the oxygen content. 7.7 g of a 10% strength aqueous solution of 2,2'-azobis(2-amidinopropane) dihydrochloride are added at a content of 1.5 ppm of $O_2$, 2.6 g of a 1% strength $H_2O_2$ solution are added after further introduction of $N_2$ and at an $O_2$ content of 1.3 ppm and finally 6.4 g of a 0.1% strength ascorbic acid solution are added at an $O_2$ content of 1.0 ppm. Owing to commencing polymerisation, in the course of which the temperature rises to about 65° C., a solid gel is formed which is then mechanically comminuted. 400 g of the comminuted gel are treated with 56.5 g of 50% strength sodium hydroxide solution (degree of neutralisation of the acrylic acid 74 mol %), thoroughly kneaded twice, treated with 25 g of a 1% strength aqueous solution of the compound V (R=$C_3H_7$), prepared according to Example 2, again kneaded twice, then dried at temperatures over 150° C. in a thin layer, ground and sieved.

A product is obtained characterised essentially, inter alia, by the following physical data, all measured in 0.9% NaCl. Extractable contents (1 h value)=2.1%, absorption under pressure (20 g/$cm^2$)=29.8 g/g.

EXAMPLE 8

0.23 g of the compound IV (R=$CH_3$), prepared according to Example 1, dissolved in 40 g of water is added to 300 g of a comminuted 30% strength polymer gel, neutralised to 73 mol %, having a monomer composition of 99.7% by weight of acrylic acid and 0.3% by weight of triallylamine, prepared analogously to Example 5, and the mixture is kneaded until homogeneous, comminuted, dried at 180° C. to a residual moisture of 3%, ground and sieved.

EXAMPLE 9

The procedure is completely analogous to Example 8, only 0.46 g of the compound IV (R=$CH_3$), prepared according to Example 1, is employed.

EXAMPLE 10

The procedure is completely analogous to Example 8, only 0.23 g of the compound V ($R=C_3H_7$), prepared according to Example 2, is employed.

EXAMPLE 11

The procedure is completely analogous to Example 8, only 0.46 g of the compound V ($R=C_3H_7$), prepared according to Example 2, is employed.

EXAMPLE 12

The procedure is completely analogous to Example 8, only 1.00 g of the compound VII (R=phenyl), prepared according to Example 4, is employed.

The resulting products of Examples 8 to 12 are characterised by the following data summarised in Table I:

TABLE I

| Example | Extractable contents 16 h value (%) | Absorption under pressure (20 g/cm$^2$) (g/g) | Gel strength* (Pa) |
|---|---|---|---|
| Starting polymer untreated | 11.8 | 8.4 | 510 |
| 8 | 9.4 | 11.0 | 600 |
| 9 | 8.6 | 22.6 | 3250 |
| 10 | 8.4 | 22.2 | 3100 |
| 11 | 8.3 | 28.0 | 3500 |
| 12 | 8.1 | 29.6 | 3700 |

All values are measured in 0.9% strength NaCl.
* = measured after a swelling time of 24 hours in 4.75% strength concentration

EXAMPLE 13

0.2% by weight of the compound V ($R=C_3H_7$), prepared according to Example 2, in 10% strength aqueous solution in a PETTERSON & KELLY mixer is sprayed onto a commercial, partly neutralised, crosslinked polyacrylic acid warmed to 45° C. for use as a super-absorber in baby nappies and the mixture is mixed for 10 min. After cooling to room temperature, the following improved values, listed in Table II, are found in comparison to the starting material:

TABLE II

| | Extractable contents 16 h value (%) | Absorption under pressure (20 g/cm$^2$) (g/g) | Gel strength* (Pa) |
|---|---|---|---|
| Starting material employed | 7.1 | 8.3 | 1500 |
| Example 13 | 6.1 | 27.4 | 3100 |

All values are measured in 0.9% strength NaCl.
*measured after a swelling time of 24 hours in 2.5% strength concentration

EXAMPLE 14

100 g of high molecular weight, non-crosslinked polyacrylic acid having a degree of neutralisation of 53 mol % in the form of a comminuted gel, prepared analogously to Example 5 *without* crosslinker is kneaded until homogeneous with 120 g of guar flour and 100 g of 0.15% aqueous solution of the compound IV, prepared according to Example 1, and the mixture is comminuted, dried in a stream of air at 180° C. for 15 min., ground and sieved. A water-swellable product having a water absorption capacity of several times its own weight is obtained.

In Examples 15 to 21, listed in Table III, the preparation of water-swellable products having good absorption ability by crosslinking of polymers of varying origin with compounds according to the invention is described, which is carried out by making the polymers into a paste in water, treating with the crosslinker, kneading until homogeneous, drying in a stream of air at 180° C., grinding and sieving.

TABLE III

| Example | Polymer | Compound according to the invention, prepared according to Ex. | | Charge in % by weight |
|---|---|---|---|---|
| 15 | Guar flour, type 6382 | IV | 1 | 0.5 |
| 16 | Commercial hydroxyethylcellulose | IV | 1 | 0.5 |
| 17 | Commercial hydroxyethylcellulose | VII | 4 | 0.7 |
| 18 | Commercial carboxymethylhydroxypropyl guar | IV | 1 | 0.5 |
| 19 | Commercial cationically modified guar | V | 1 | 0.5 |
| 20 | Commercial Na alginate | IV | 1 | 0.5 |
| 21 | RHODIGEL[1] | IV | 1 | 0.5 |

[1]: Polymer from RHONE POULENC

EXAMPLE 22

600 ml of hexane are introduced into a 1 l glass polymerisation flask provided with a stirrer, thermometer and reflux condenser, and 98.9 g of acrylic acid and 1.1 g of the compound VI ($R=CH=CH_2$), prepared according to Example 3, are dissolved therein. While passing in a gentle stream of $N_2$, the flask is heated to 68° C. by means of an electrically heated water bath, whereupon the addition of 1.0 g of dilauryl peroxide is carried out. After the polymerisation commences, reflux clearly occurs and the polymer formed flocculates. The mixture is subsequently stirred under reflux for 3 hours, and the polymer is then filtered off with suction and dried to constant weight in a drying oven. 100 g of a white powder are obtained, which can be employed as an acidic thickener in cosmetic preparations.

EXAMPLE 23

600 ml of tert-butanol are introduced into a 1 l glass polymerisation flask provided with a stirrer, thermometer, reflux condenser, gas inlet tube and electrically heated water bath, and 0.1 g of the compound VII (R=phenyl), prepared according to Example 4, and 65 g of acrylamido-2-methyl-propanesulphonic acid (AMPS) are suspended therein with stirring. About 5.5 g of ammonia gas are then passed in via the gas inlet tube, a slightly turbid solution being formed. The pH of this solution must be >7. 15 g of acrylamide and 20 g of N-vinyl-N-methylacetamide are then added and the solution is heated to a temperature of 50° C. while passing in a gentle stream of $N_2$. 1.0 g of azodiisobutyronitrile is added as initiator and the stirring speed is restricted to 60–80 rpm. After about 10 min., the polymerisation commences, which can be ascertained from a flocculation of the polymer and a temperature rise. In the course of about 20 min., a thick paste is formed and the temperature rises to about 75° C. After reaching the maximum temperature, the mixture is subsequently stirred at 80° C. for 2 hours, and the polymer is filtered off with suction and dried to constant weight in a vacuum drying oven at 60° C. 105 g of white powder having a bulk density of about 0.2 kg/l are obtained, which is outstandingly suitable as an additive in drilling muds and cement slurries in natural gas and oil exploration.

EXAMPLE 24

A 10% strength aqueous copolymer solution having the monomer composition 90% by weight of acrylic acid and 10% by weight of vinylphosphonic acid, partially neutralised with NaOH to a pH of 5.5-6.0 and treated with 1.0% by weight (relative to polyacrylic acid) of the compound V, prepared according to Example 2, is suitable for use as a binder/strengthener of non-wovens, combined with the advantage of better absorptive power. For this purpose, it is sprayed uniformly onto both side of an absorbent pad of cellulose fluff (about 6×20×1.5 cm/b×l×h) in such a way that the absorbent pad is loaded with 1% of the polymer solid, relative to the dry weight of the absorbent pad. After storage at room temperature in air for 24 hours or a corres-ponding shorter residence time at higher temperatures, the absorbent pads thus treated were examined for strength and absorptive capacity against corresponding untreated absorbent pads. The strength was tested by exposing the absorbent pads to a defined stream of air in a special vortexing vessel. The components separated from the absorbent pad by the vortexing were sucked off through a screen of defined mesh width. The content of undestroyed pad material not sucked off and remaining in front of the screen was then determined in % relative to the starting weight.

The suction capacity was determined as follows: the absorbent pad, lying flat on a screen, was immersed in 0.9% strength NaCl solution for one minute. The screen was then taken out and allowed to drip for one minute. For this purpose, the experimental arrangement was inclined at about 45° C. The weight increase per gram of absorbent pad was calculated.

It was possible to determine an improvement of about 20% with respect to strength for the treated absorbent pads in comparison with the untreated pads, and of about 10% with respect to absorbent capacity.

What we claim:

1. Water-swellable hydrogel essentially derived from one or more monomers of the following group acrylic acid, methacrylic acid, crotonic acid, 2-acrylamido-2-methylpropane-sulphonic acid or -phosphonic acid, vinylphosphonic acid, vinylphosphonic acid half-esters, their salts, acrylamide, N-vinylamides or mixtures thereof in copolymerized form, which hydrogel further comprises a compound of the general formula

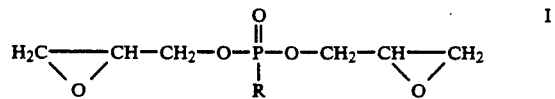

in which R denotes $(C_1-C_6)$-alkyl, $(C_3-C_8)$-cycloalkyl, a group of the general formula II

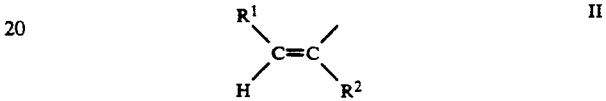

in which $R^1$ and $R^2$ independently of one another represent hydrogen of $(C_1-C_4)$-alkyl or a group of the general formula III

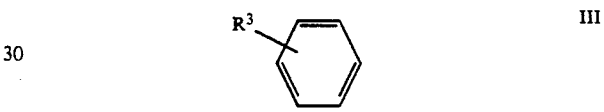

in which $R^3$ represents hydrogen, halogen or $(C_1-C_4)$-alkyl.

2. Water-swellable hydrogel according to claim 1 wherein R is $(C_1-C_3)$-alkyl.

3. Water-swellable hydrogel according to claim 1 wherein $R^1$ and $R^2$ denote hydrogen.

4. Water-swellable hydrogel according to claim 1 wherein $R^3$ denotes methyl or chlorine.

5. Water-swellable hydrogel according to claim 1 wherein $R^3$ denotes hydrogen.

* * * * *